US00PP07927P

United States Patent [19]

Cobia et al.

[11] Patent Number: Plant 7,927

[45] Date of Patent: Jul. 28, 1992

[54] CACTACEAE PLANT NAMED 'WINDSOR'

[76] Inventors: Barnell L. Cobia; Mark E. Cobia, both of P.O. Box 771369, Winter Garden, Fla. 34777-1369

[21] Appl. No.: 621,066

[22] Filed: Dec. 3, 1990

[51] Int. Cl.[5] ..... A01H 5/00

[52] U.S. Cl. ..... Plt./88.5

[58] Field of Search ..... Plt./88

[56] References Cited

U.S. PATENT DOCUMENTS

P.P. 3,690 3/1975 Cobia ..... Plt. 88

P.P. 4,201 1/1978 Cobia et al. ..... Plt. 88

*Primary Examiner*—James R. Feyrer

*Attorney, Agent, or Firm*—Roger L. Martin

[57] ABSTRACT

A new and distinct plant variety of the Cactaceae family that is of the type known commercially as a "Christmas Cactus" has a growth habit which is similar to that of the "Lavender Doll" variety but which, nevertheless, differs among other things, by having phylloclades with shorter midribs, flowers that have wider tube forming tepals, a longer perianth tube with larger major and minor axes as well as longer styles and ovaries.

4 Drawing Sheets

BACKGROUND OF THE INVENTION

The invention relates to a new and distinct variety of the Cactaceae family which has been named *Zygocactus truncatus* 'Windsor' by the inventors.

Certain plant varieties of the Cactaceae family are well known in the foliage plant market and among these are those which are commonly referred to as the Christmas cactus varieties because they tend to bloom during the Thanksgiving-Christmas holiday season in the northern hemisphere.

The Christmas Cactus Varieties on the market have blooms which vary in color from one variety to the next as is evident from the current U.S. patent art. One of the more popular varieties sold commercially in the market place is the variety that has been named *Zygocactus truncatus* 'Lavender Doll'. It forms the subject matter of U.S. Plant Pat. No. 3,690. The new "Windsor" variety and the "Lavender Doll" variety have a common ancestor in the unpatented variety known in the trade as "Christmas Cheer".

SUMMARY OF THE INVENTION

A general objective has been to develop a new plant variety which is distinguishable from the "Lavender Doll" variety and which is capable of being marketed competitively therewith.

The objective has been fully realized by the development of the new plant variety hereinafter described in detail. The new plant variety was developed in a nursery location at Winter Garden, Fla. from a mutation that appeared on an unnamed research variety designated "ZH4692M2". The research variety was under cultivation in a designated research area at the nursery location referred to above and was developed from a natural mutation that appeared on a variety known as "Lavender Lady" (see: U.S. Plant Pat. No. 4,201). The "Lavender Doll" and "Lavender Lady" varieties are both descendents of and two generations removed from the "Christmas Cheer" variety.

Through successive propagations of cuttings taken from the mutated plant part that appeared on the research variety, it has been ascertained that specimens of the new plant variety generally resemble the "Lavender Doll" variety but are distinguishable from this variety and other related varieties known to the inventors by a growth habit which is evident in plant specimens of the new variety that have been propagated and grown under nursery conditions utilized in the growing of tropical plants in the Winter Garden, Fla. area as combining the following principal characteristics:

1. A more erect posture at maturity than the 'Lavender Doll' variety.

2. Phylloclades which, in comparison to the 'Lavender Doll' variety, have midribs with generally shorter length dimensions.

3. Flowers which, in comparison to the 'Lavender Doll' variety, have (a) a tube forming tepal series with generally greater maximum blade width dimensions, (b) a perianth tube with generally longer length dimensions, as measured along the axis of the tube, (c) a perianth tube with generally longer major elliptical axis dimensions at the interior of the throat and generally longer minor elliptical axis dimensions at the interior of the throat, and a gynoecium (pistil) with generally longer style length dimensions as measured between the proximal and distal ends, and (e) ovaries with generally longer length dimensions as measured from the insertion to the concavity base.

BRIEF DESCRIPTION OF THE DRAWINGS

The accompanying drawings serve by color photographic means to illustrate the new plant variety and wherein one sheet shows a twenty-four (24) month old specimen which was grown from the propagation of a single phylloclade in a conventional 3½ in. pot found in the market place.

A second sheet shows an enlargement of a fully open bloom taken from the specimen shown in the first mentioned sheet.

Still another sheet shows another fully open bloom that has been sectioned generally longitudinally through the perianth tube and the ovary to expose the style and stamen arrangement.

The last sheet show a group of four phylloclades taken from a specimen of the new variety, each phylloclade having an attached bud or bloom to illustrate the progressive stages of maturity of the buds, the progree being shown in a clockwise direction beginning in the upper left portion of the illustrated group.

DETAILED PLANT DESCRIPTION

The following is a detailed description of the new plant variety with colors and hues, unless otherwise clearly indicated by the text, as for example, through the absence of color notations, being named in accord with the ISCC-NBS Method of Designating Colors (U.S. Dept. of Commerce, National Bureau of Standards, Circular 553), the named colors being interpreted from color notations derived by comparison with color specimens of the Munsell Book of Color. The description is further based on observations of well fertilized plants about two years old from initial propagation of a single phylloclade and which were grown under 50–75% shaded glasshouse nursery conditions in the Winter Garden, Fla. area wherein temperatures range from 60°–85° F. during the winter months, from 75°–95° F. during the summer months, and are ambient during the intervening periods.

I. Name: *Zygocactus truncatus* 'Windsor'.

II. Derivation: The new variety was developed from a mutation that occured on an unnamed research variety designated as ZH4692M2. This research variety has characteristics which are similar to those of "Lavender Doll" but may, among other things, be distinguished therefrom by greater pedal widths.

III. Classification:

A. *Botanic* (*Britton and Rose, The Cactaceae,* Constable and Co., Ltd., London 1937, Vol. IV)-.—(1) Family: Cactaceae. (2) Tribe: Cereeae. (3) Sub-tribe: Epiphyllanae. (4) Genus: Zygocactus. (5) Species: *truncatus* (Haworth) Schumann.

B. *Commercial.*—Thanksgiving-Christmas blooming cactus.

IV. Stems:

A. *General.*—Irregular with usually multichotomous branching of both upright and pendulous, adventitiously rootable, flattened phylloclades that have a prominent midrib and prominently toothed lateral wings.

B. *Phylloclades.*—(1) General: Elongated and flat with a transversely elongated, areole bearing, truncated apex, with inwardly tapering basal wing margins that merge with a usually broadly pointed basal juncture with the phylloclade therebelow, and with an axially located areole usually being associated with each tooth. (2) Midrib: (a) General — Extends longitudinally of phylloclade and continuously through joints and with a laterally tapering cortex at the wing insertions. Pith surrounding vascular bundles that branch and provide lateral extensions of the vascular system to the marginal teeth. (b) Texture — Smooth, waxy epidermis with wax in small embedded scales and becoming woody in basal stem areas with specimen aging.(c) Size (at maturity) — 1. Length: Usually 35–50 mm. (Mean=42.8 mm). (Dev.=3.93 mm). 2. Thickness: Usually 2–6 mm. (Mean=3/6 mm). (Dev.=3.93 mm). (d) Color (at maturity) — Usually dominated by a yellow green and/or olive green hue. Commonly moderate yellow green (7.5 GY 5/6) and/or moderate olive green (7.5 GY 4/6). (3) Wings: (a) General — Dentate and generally flattened from midrib cortex to tooth insertions and with slight thinning taper toward margins. (b) Margins — Toothed. (c) Texture — Succulent to leathery with smooth, waxy epidermis where the wax is arranged in small embedded scales of higher density than in midrib area, and becoming corky in the basal stem areas with specimen aging. (d) Size (at maturity) — 1. Thickness: About 1.0–2.5 mm in the area intermediate the margin and midrib. (Mean=1.7 mm). (Dev.=0.40 mm). 2. Width: Usually 13–21 mm as measured from phylloclade axis to most offset lateral areole. (Mean=16.8 mm). (Dev.=1.77 mm). (e) Color (at maturity) — Usually dominated by an olive green hue. Commonly moderate olive green (7.5 GY 4/6) (7.5 GY 4/4) (7.5 GY 3/4). (4) Teeth: (a) Shape — 1. General: Generally flattened and taperedalong the margins and from the wing insertion to an apex having a hyaline, single cell, pointed spine with nonpredictable bending. 2. Adaxial margin: Usually straight to convex. 3. Abaxial margin: Usually straight to concave. (b) Orientation — Usually project distally of phylloclade in an alternate arrangement. (c) Margins — Entire. (d) Texture — Succulent to leathery with smooth waxy epidermis having wax in small embedded scales of density comparable to wings, and becoming corky in basal stem areas with specimen aging. (e) Size (at maturity) — 1. Thickness: Usually 1.0–2.0 mm in center area. (Mean=1.3 mm). (Dev.=0.38 mm). 2. Areole to apex dimension (adaxial marginal side): Usually 5.0–11.0 mm in the upper quadrants of the phylloclade. (Mean=7.7 mm). (Dev.=1.69 mm). (f) Number — Usually 7–10 per phylloclade. (g) Color — Usually dominated by an olive green hue. Commonly moderate olive green (7.5 GY 3/4)(7.5 GY 4/4). (5) Areoles: (a) Terminal areole — Large, elongated, oval shaped with several acicular bristles, andseveral buds that may mature into either new phylloclades or flowers. The opposite ends of the areole are located adjacent to subsidiary areoles which are in turn located at the axils of the teeth at the distal end of the phylloclade. (b) Axillary areoles — Acicular bristles without glochida but having copious, short, brownish, multicellular, wooly hairs. In areoles located below the teeth at the distal end of the phylloclade, there is usually only one areole which is frequently latent.

V. Buds: Unarmored, ovoid and chlorophyllous.

VI. Flowers:

A. *General.*—Sessile, zygomorphic, usually solitary, terminal, perfect and epigynous with double hypanthium and whorled tepals (undifferentiated sepals and petals) having a spiral emergence as a perianth provided with a sepaloid series of free tepals, a tube laminating series of tepals, and a tube forming series of united tepals.

B. *Sepaloid series.*—(1) General: Free tepals inserted on top of ovary. (2) Shape: Deltoid in outer members of whorl and grading inwardly in the whorl to provide progressively greater length dimensions and broader apices. All members have a pointed tip and entire margins with sparse irregular teeth appearing mainly in the apex areas of the inner members of the whorl.(3) Texture: Succulent and glabrous outer whorl members and grading inwardly in whorl to silken blades with fleshy basal areas. (4) Numbers: Usually 6–8. (5) Size (at full bloom): (a) Length (base-tip dimension) — Usually less than 23 mm. (Mean=11.5 mm). (Dev.=5.53 mm). (b) Width (maximum) — Usually less than 16 mm. (Mean=9.8 mm). (Dev.=2.90 mm). (6) Color (at full bloom): Varies from the outer members to the inner members with the smallest outer whorl tepals usually having a continuous field that in color is dominated by a yellow green hue. The inner whorl tepal members have marginal blade areas that in color are dominated bypurplish pink and/or reddish purple hues, the marginal color projecting proximally to merge with the distally projecting color in the basal area and which is usually dominated by a yellow green hue. Commonly moderate purplish pink (2.5 RP 7/6) and/or light reddish purple (2.5 RP 6/8) in the marginal areas of the inner whorl members and brilliant yellow green (2/5 GY 8/10)(2.5 GY 8/8) and/or strong yellow green (2.5 GY 7/8) in the center field and basal areas of the inner whorl members. Commonly strong yellow green (2.5 GY 6/8) and/or moderate yellow green (2.5 GY 6/6) in the outermost members of the whorl. (7) Orientation: Erect to recurve at full bloom.

C. *Tube laminating series.*—(1) General: Tepals inserted on ovary and becomingbasally united below the throat as outer laminations on the perianth tube and with progressively greater amount of basal fusion inwardly in the whorl. (2) Shape: Zygomorphic and grading inwardly in the whorl with progressively greater length dimensions and broader apices so that the blade area changes inwardly in the whorl from widely obovate in outer whorl members to obovate in the inner whorl members. Tips vary from accute to rounded or obtuse. Margins are entire to fimbriolate with sparse, irregular teeth mainly in apex areas. (3) Texture: Succulent and glabrous outer whorl members and grading inwardly to silken blades with slightly fleshy basal areas. (4) Number: Usually 5–9 tepals. (5) Size (at full bloom): (a) Length (base-tip dimension) — Usually 18–63 mm. (Mean=38.4 mm). (Dev.=13.85 mm). (b) Width (maximum) — Usually 11–21 mm. (Mean=16.7 mm). (Dev.=2.32 mm). (6) Color (at full bloom): (a) General — Tepals with basal areas that in color are white and/or dominated by a purplish pink, reddish purple and/or yellow green hue immediately above insertion and marginal and center field blade areas that in color are dominated by reddish purple and/or purplish pink hues which merge with the distally entending basal area colors. (b) Basal area — Commonly brilliant yellow green (2.5 GY 9/8)(2.5 GY 8/10)(2.5 GY 8/8) inthe outermost members of the whorl and becoming pale purplish pink (2.5 RP 8/4) and/or white (2.5 RP 9/0) in the inner whorl members along tube attached area. (c) Blade area — Commonly strong reddish purple (2.5 RP 5/10), deep purplish pink (2.5 RP 6/8) and/or moderate purplish pink (2.5 RP 7/6). (d) Orientation: Perpendicular to recurve at full bloom.

D. *Tube forming series.*—(1) General: Tepals basally united to form hollow perianth tube that is inserted on ovary and equipped at its throat with an irregular carina (keel). (2) Shape: (a) Perianth tube — Elongated and ellipsoidal in cross section with the major ellipsoidal axis usually being generally normal to the plane of the supporting phylloclade. (b) Bloom — Nearly zygomorphic and elliptic with acute to rounded or slightly obtuse tips. Margins entire to fimbriolate and having sparse irregular teeth in apex area. (c) Carina (keel) — Irregular and transcending. (3) Texture: (a) Perianth tube — Thick, succulent and slightly ribbed. (b) Blades — Translucent and silken. (c) Carina (keel) — Fleshy. (4) Number: Usually 8–9. (5) Size (at full bloom):(a) Perianth tube — 1. Length (base-keel): Usually 33–45 mm along tube axis. (Mean=39.3 mm). (Dev.=2.97 mm). 2. Major axis: Usually 14–18 mm at throat interior. (Mean=16.0 mm). (Dev.=1.05 mm). 3. Minor axis: Usually 8–14 mm at throat interior. (Mean=10.3 mm). (Dev.=1.68 mm). (b) Blades — 1. Length (keel-tip): Usually 26–35 mm. (Mean=30.5 mm). (Dev.=2.20). 2. Width (maximum): Usually 14–23 mm. (Mean=18.4 mm). (Dev.=2.34 mm). (6) Color (at full bloom): (a) Perianth tube — A basic fluid that is white with longitudinally extending, randomly arranged striations or streaks that in color are dominated by a purplish pink hue. Commonly white (2.5 RP 9/0) with random striations of pale purplish pink (2.5 RP 8/4). (b) Blades — Marginal and center field areas that are nearly uniform in color distally of the keep and dominated by a reddish purple hue, the color merging proximally with a basal area color that is white or dominated by a purplish pink hue. Commonly light reddish purple (2.5 RP 6/8) and/or strong reddish purple (2.5 RP 5/10) in marginal and center field areas. Commonly pale purplish pink(2.5 RP 8/4) and/or white (2.5 RP 9/0) in basal area. (c) Carina (keel) — Color dominated by a reddish purple hue. Commonly strong reddish purple (2.5 RP 4/10)(2.5 RP 5/10). (7) Orientation: Perpendicular to recurve.

E. *Androecium (stamens).*—(1) General: Numerous exserted and diadelphous stamens with one group having filaments basally fused to the perianth tube and the other group having filaments basally united to form a nectary housing, thin annulus around the style and which is provided with thin, deflexed, irregular, toothed margin or ruffle at the throat of the annulus. (2) Stamen number: (a) Tube attached group — Usually 70–105. (b) Basally united group — Usually 15–22. (3) Filaments: (a) General — Translucent with anther connective. (b) Shape — Long, slender, terete. (c) Texture — Glabrous and capillaceous. (d) Color — Commonly white (2.5 RP 9.5/0) over entire length. (e) Size (at full bloom) — 1. Length: (a) Tube attached group — Usually 35–69 mm. (Mean=55.6 mm). (Dev.=9.31 mm). (b) Basally united group — Usually 30–60 mm. (Mean=47.3 mm). (Dev.=7.96 mm).2. Diameter: Usually about 0.5 mm intermediate opposite ends. (4) Anthers: (a) General — Adnate with four longitudinally dehiscent pollen sacs and connective inserted at end. (b) Shape — Elongated. (c) Texture — Waxy. (d) Color (before dehiscence) — Dominated by yellow hue. Commonly light yellow (2.5 Y 9/6)(5 Y 9/6).

F. *Gynoecium (pistil)*.—(1) General: Exserted with compound, pariental placentation and united style surrounded by annular diffuse yellowish nectary at its insertion. (2) Style: (a) General — Hollow, stout and inserted at ovary. (b) Shape — Elongated and terete. (c) Texture — Fleshy and smooth. (d) Color — Dominated by a purplish pink and/or purplish red hue at the basal end and progressively varying to a color dominated by a reddish purple hue at the distal end. Commonly deep purplish pink (5 RP 6/10) and/or moderate purplish red (5 RP 5/10) at basal end and strong reddish purple (2.5 RP 5/10)(2.5 RP 4/10) at distal end. (e) Size (at full bloom) — 1. Length: Usually 59–71 mm. (Mean=63.9 mm). (Dev.=3.90 mm). 2. Diameter: Generally about 1.0 mmintermediate opposite ends. (3) Stigma: (a) General — Exserted and erect with usually 6–8 inner marginally adhering lobes. (b) Shape — Elongated and tapering toward lobe tips and having relatively blunt apices. (c) Texture — Fleshy and smooth with inner sides of lobes having short glutinous capillaceous hairs. (d) Color — Dominated by purplish pink and/or reddish purple hues. Commonly moderate purplish pink (2.5 RP 7/6) and/or light reddish purple (2.5 RP 6/8). (e) Size — 1. Length: Usually 3–5 mm along inner margins. (Means=4.3 mm). (Dev.=0.64 mm). (4) Ovary: (a) General — Inferior with thin epidermis and usually 5–7 carpules with numerous ovules. (b) Shape — Terete to ovid and generally broadening from insertion to floral end. Ribbed single concavity with inserted style. (c) Texture — Succulent with glabrous thin outer epidermis. (d) Color — Usually dominated by a yellow green hue. Commonly strong yellow green (2.5 GY 6/8) and/or moderate yellow green (2.5 GY 6/6)(2.5 GY 5/6). (e) Size — 1. Length: Usually 9–13 mm from insertion to cavity base. (Mean=10.5 mm). (Dev.=1.21 mm).2. Major axis: Usually 10–12 mm at distal end of concavity. (Mean=10.8 mm). (Dev.=0.60 mm). 3. Minor axis: Usually 9–11 mm at distal end of concavity. (Mean=9.9 mm). (Dev.=0.57 mm).

GENERAL DESCRIPTION OF A PLANT SPECIMEN OF THE "WINDSOR" VARIETY

Age of plant: Twenty-four (24) months from initial propagation of single phylloclade.

Branches from propagated phylloclade: Two (2).

Total number of new phylloclades grown from propagated phylloclade: Seventy-nine (79).

| General: | | | |
|---|---|---|---|
| Branch No. | No. of Phylloclades | Max. Length | No. of Tips |
| 1 | 40 | 287 mm | 11 |
| 2 | 39 | 262 mm | 12 |

| Midribs: | | |
|---|---|---|
| Branch No. | Avg. Length | Avg. Thickness |
| 1 | 41.9 mm | 4.8 mm |
| 2 | 42.5 mm | 4.8 mm |

| Wings: | | |
|---|---|---|
| Branch No. | Avg. Center Thickness | Avg. Max. Width |
| 1 | 2.0 mm | 14.8 mm |
| 2 | 1.9 mm | 15.7 mm |

-continued

| Teeth: | | | |
|---|---|---|---|
| Branch No. | Avg. No. Phylloclade | Avg. Center Thickness | Avg. Areole to Apex length |
| 1 | 7.9 | 1.3 mm | 6.8 mm |
| 2 | 7.8 | 1.2 mm | 7.0 mm |

Phylloclade color: Moderate yellow green (7.5 GY 5/6) and moderate olive green (7.5 GY 4/6)(7.5 GY 4/4).

GENERAL DESCRIPTION OF A FLOWER OF THE "WINDSOR" VARIETY

Age of flowering plant: Twenty-four (24) months.

Month of blooming: December.

Place of blooming: Winter Garden, Fla. under shaded greenhouse nursery conditions.

No. of buds and blooms on flowering plant: Twenty-one (21).

Bloom life: Seven (7) days.

Sepaloid series of tepals:

*Number.*—7.

*Size (at full bloom)*.—Maximum base-tip dimension: 20 mm. Minimum base-tip dimension: 6 mm. Maximum width dimension: 15 mm.

*Color (at full bloom)*.—Strong yellow green(2.5 GY 6/8) and moderate yellow green (2.5 GY 6/6) in continuous filed of outer whorl members of small tepals. Moderate purplish pink (2.5 RP 7/6), light reddish purple (2.5 RP 6/8) in marginal areas and brilliant yellow green (2.5 GY 8/10)(2.5 GY 8/8) in the center field and basal areas of the inner whorl members.

Tube laminating series of tepals:

*Number.*—6.

*Size (at full bloom)*.—Maximum base-tip dimension: 63 mm. Minimum base-tip dimension: 30 mm. Maximum blade width: 21 mm. Minimum blade width: 17 mm.

*Color.*—Strong reddish purple (2.5 RP 5/10), deep purplish pink (2.5 RP 6/8) and moderate purplish pink (2.5 RP 7/6) in marginal and center field areas of the blades and pale purplish pink (2.5 RP 8/4) and white (2.5 RP 9/0) in the basal areas of the blades.

Tube forming series of tepals:

*Size (at full bloom)*.—Perianth tube: Length (base to keel) — 45 mm along tube axis. Major axis — 18 mm at throat interior. Minor axis — 11 mm at throat interior.Blades: Maximum length (keel-tip) — 35 mm. Minimum length (keel-tip) — 33 mm. Maximum blade width — 23 mm. Minimum blade width — 19 mm.

*Color.*—Perianth tube: A major field of white (2.5 RP 9/0) with random striations of pale purplish pink (2.5 RP 8/4). Blades: White (2.5 RP 9/0) in basal areas of blades and light reddish purple (2.5 RP 6/8) and strong reddish purple (2.5 RP 5/10) in marginal and center field areas of the blades.

Anderoecium:

*Stamen number.*—Tube attached group: 102. Basally united group: 19.

*Filaments.*—Color: White (2.5 RP 9.5/0) over entire length. Size (at full bloom): Length — Tube attached group: 65 mm (avg.). Basally united group: 52 mm (avg.). Diameter — About 0.5 mm intermediate the opposite ends.

*Anthers.*—Color (before dehiscing) Light yellow (2.5 Y 9/6).

Gynoecium (pistil):

*Style.*—Color: Deep purplish pink (5 Rp 6/10) and moderate purplish red (5 RP 5/10) in basal area and strong reddish purple (2.5 RP 5/10) (2.5 RP 4/10) in distal area.

We claim:

1. A new and distinct plant variety of the Cactaceae family as shown and described herein and which is mainly distinguished from its antecedents and known related varieties by growth characteristics that are similar to those of the "Lavender Doll" variety but as modified by the combination of characteristics which follows:

(1) a more erect posture at maturity than the "Lavender Doll variety, (2) phylloclades which, in comparison to the "Lavender Doll" variety, have midribs with generally shorter length dimensions, (3) flowers which, in comparison to the "Lavender Doll" variety, have (a) a tube forming tepal

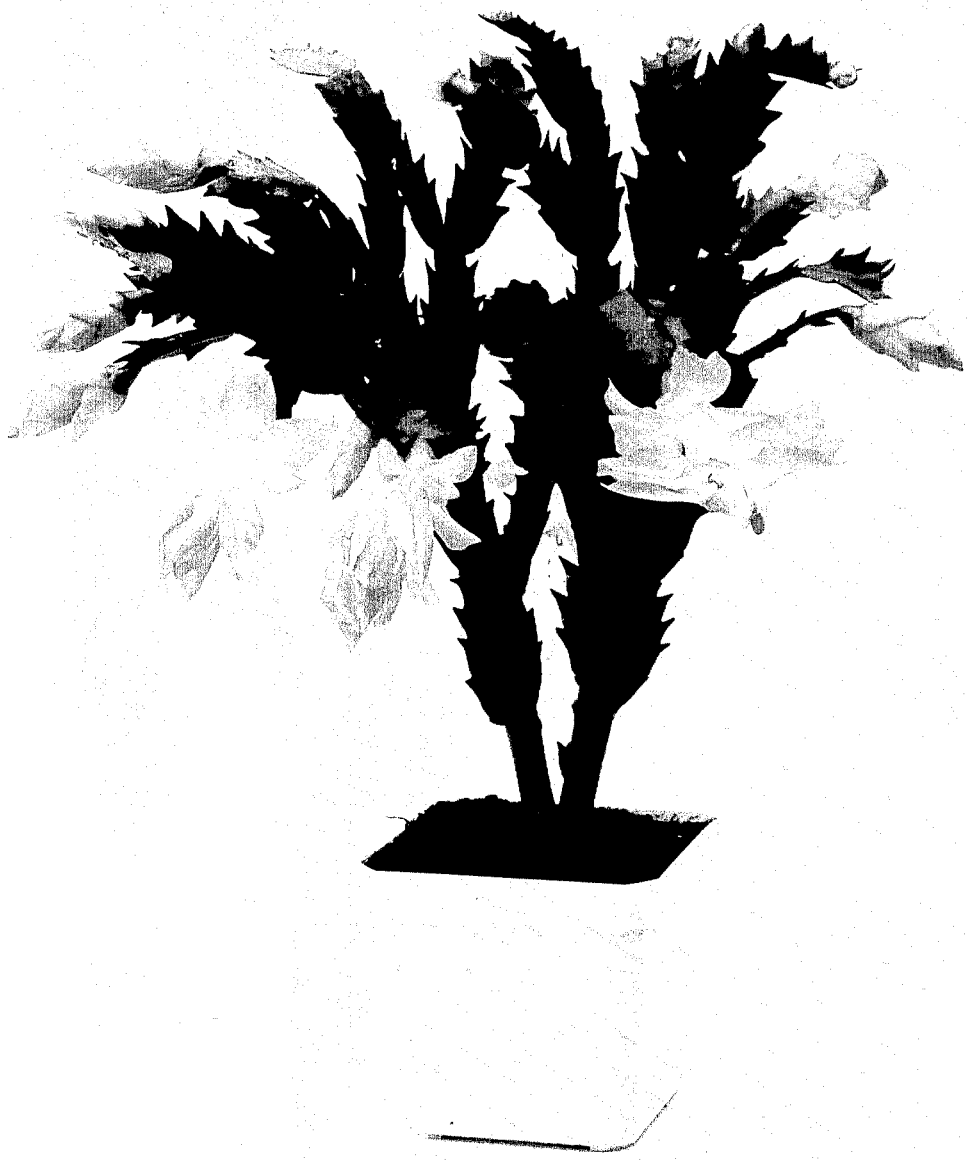

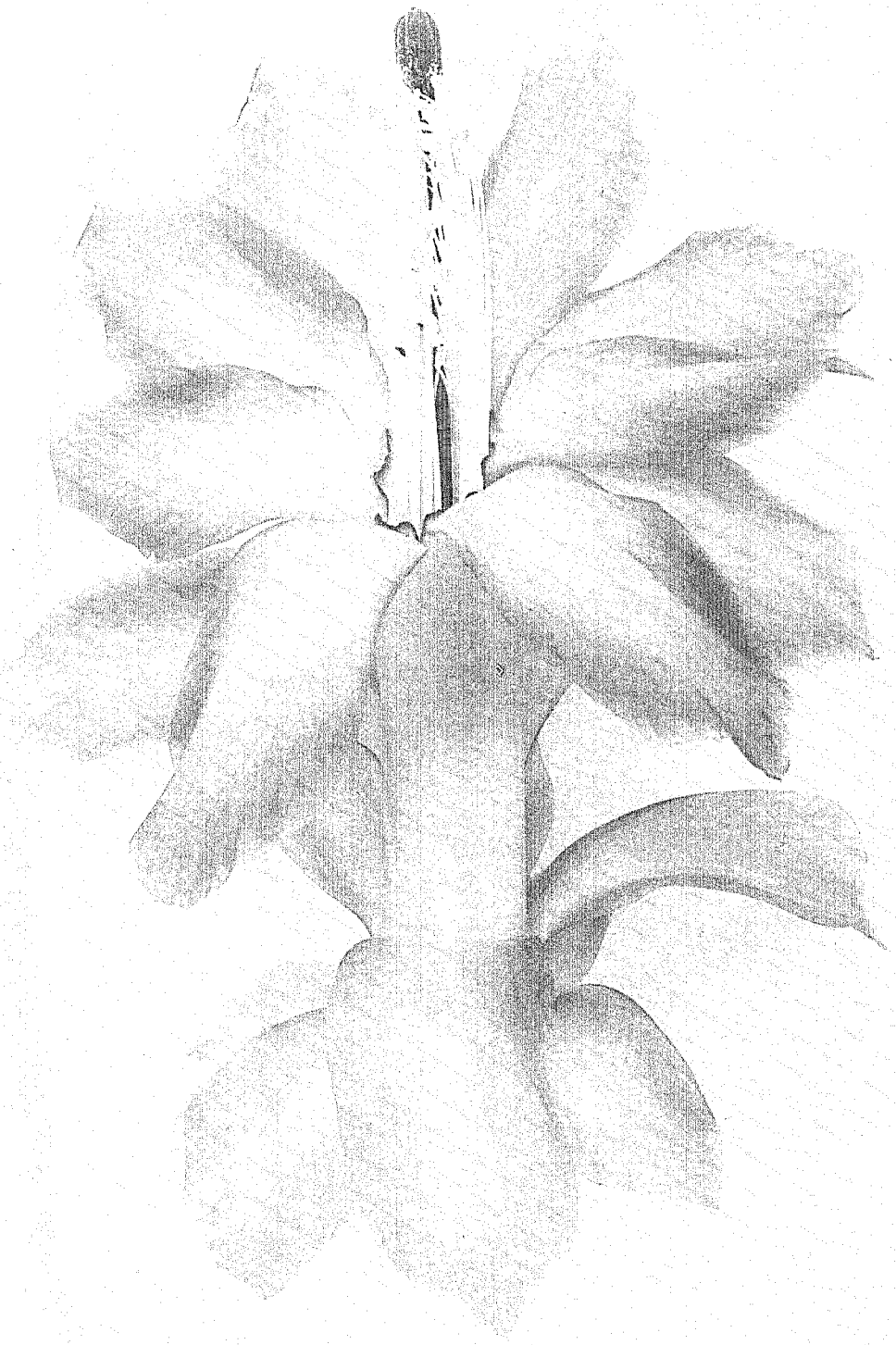

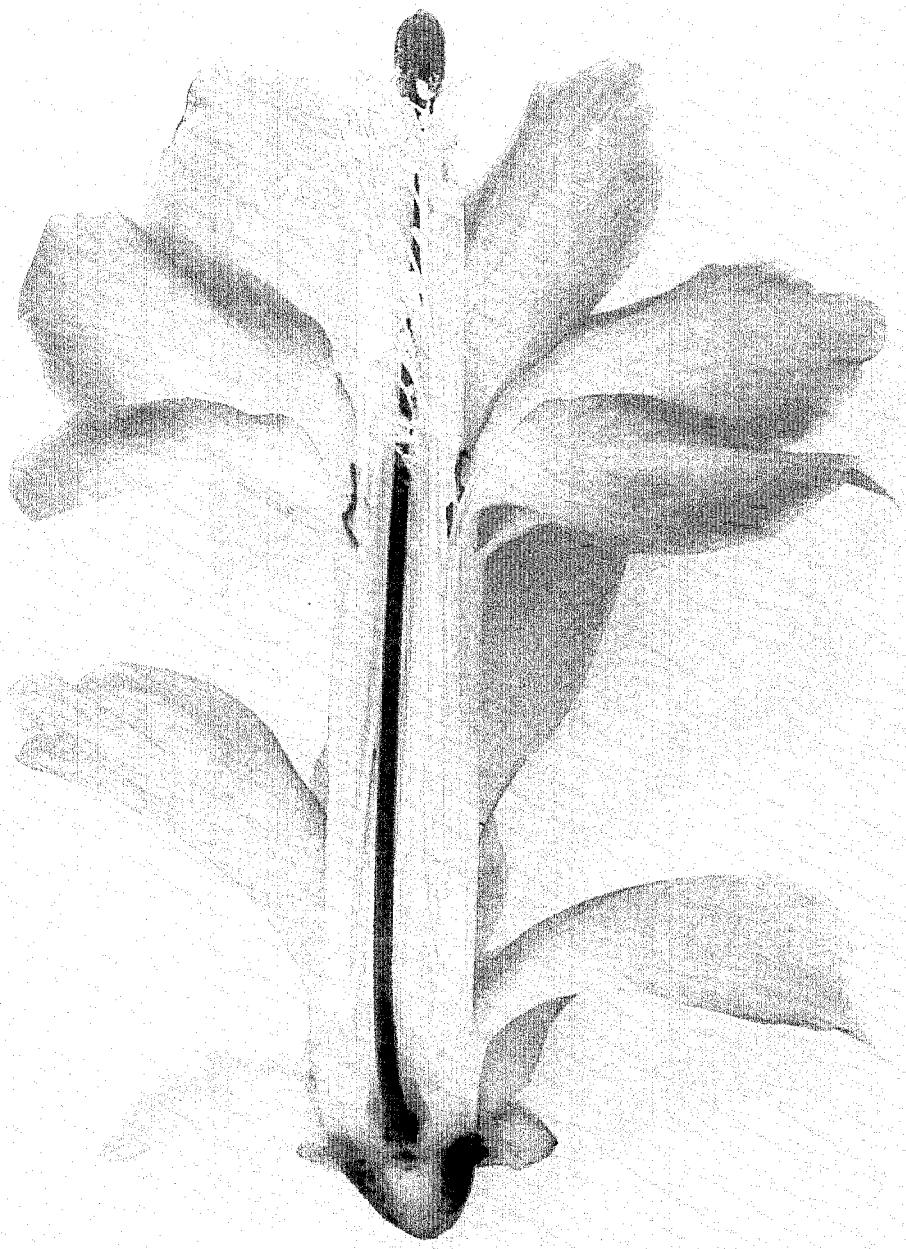

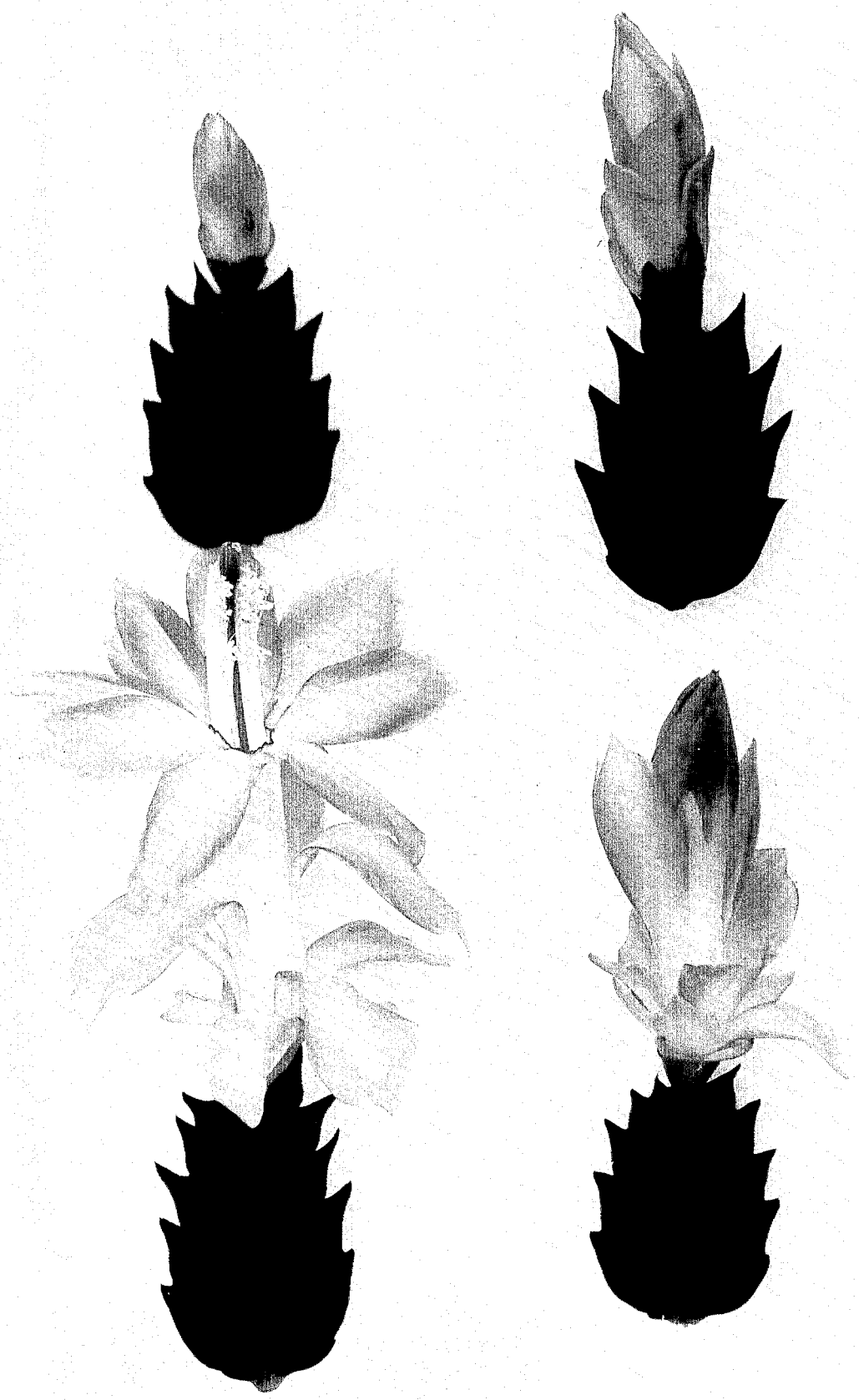

* * * * *